United States Patent [19]

Sedlacek

[11] 4,261,352
[45] Apr. 14, 1981

[54] ADJUSTABLE DIAPHRAGM

[76] Inventor: Cynthia L. Sedlacek, Deposit, N.Y.

[21] Appl. No.: 25,375

[22] Filed: Mar. 30, 1979

[51] Int. Cl.³ .............................................. A61F 5/46
[52] U.S. Cl. .................................................. 128/127
[58] Field of Search ............................... 128/127–130, 128/138 R

[56] References Cited

U.S. PATENT DOCUMENTS

| 2,664,082 | 12/1953 | Heuboski et al. | 128/127 |
| 3,117,573 | 1/1964 | Snell | 128/127 |
| 3,659,597 | 5/1972 | Wolfers | 128/130 |
| 3,744,489 | 7/1973 | Munro | 128/130 |

FOREIGN PATENT DOCUMENTS 414541 6/1925 Fed. Rep. of Germany ........... 128/127

Primary Examiner—C. Fred Rosenbaum
Attorney, Agent, or Firm—Richard G. Stephens

[57] ABSTRACT

An adjustable contraceptive diaphragm includes a sheath having a rim surrounding a telescoping resilient ring. An outer ring member of generally U-shaped cross-section surrounds the rim of the sheath, and clamps against opposite sides of the sheath, and one end of the outer ring member telescopes into the other end and can be fastened at selected discrete telescoped positions.

7 Claims, 8 Drawing Figures

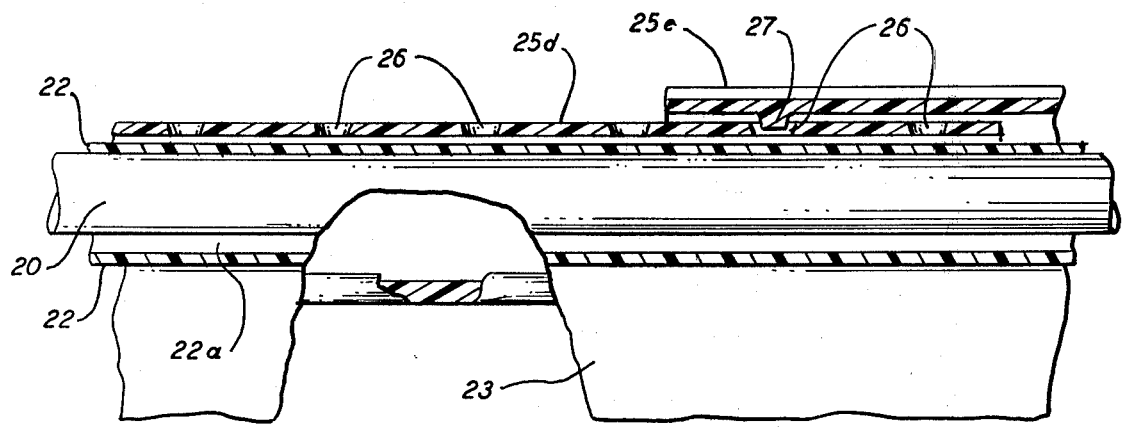
FIG. 6
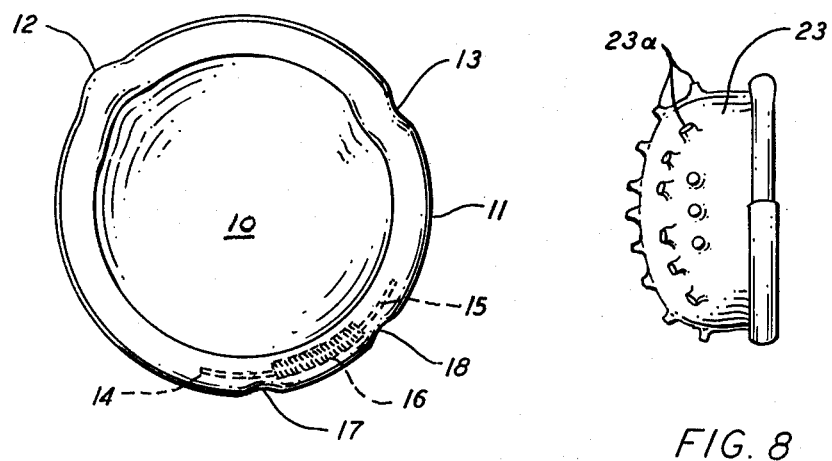
FIG. 7
Prior Art
FIG. 8

ADJUSTABLE DIAPHRAGM

My invention relates to contraceptive devices, and more particularly, to an improved adjustable pessary or diaphragm. Some advantages of a vaginal diaphragm which is diametrically adjustable have been recognized. Several forms of adjustable diaphragm have been proposed, two such devices being shown in U.S. Pat. Nos. 2,443,943 and 2,463,356. However, so far as I am aware, no adjustable vaginal diaphragm has gained significant commercial acceptance. A general object of the present invention is to provide an improved vaginal diaphragm which is diametrically adjustable.

A diaphragm may be deemed inoperative and perhaps worse than useless if it does not reliably prevent the passage of sperm to the cervical canal. An important specific object of the present invention is to provide an improved adjustable diaphragm which is more effective or reliable in blocking the passage of sperm than prior adjustable diaphragms. Another object of the invention is to provide an improved adjustable diaphragm which does not cause damage or irritation to delicate internal female tissue. A further object of the invention is to provide an improved adjustable diaphragm which can be easily adjusted by an unskilled person to a desired diameter. Another object of the invention is to provide an improved diaphragm which is adjustable over a greater range of diameters than prior art devices. A further object of the invention is to provide an improved diaphragm which lends itself to accurate discrete diametrical adjustment. Yet another object of the invention is to provide an improved adjustable diaphragm which will not vary from its intended diameter while it is being installed, or accidentally misadjusted while it is being stored in between the occasions on which it is used. Some prior art diaphragms, including those shown in the two mentioned patents, are adjustable in the sense that springs within them may be expanded or compressed to allow a change in diameter when the device is inserted into the user's vagina; however, they disadvantageously apply a spring force to the user's vaginal areas which is proportional to how much the springs have been compressed. If a user finds the spring forces great enough to cause irritation, she can reduce them only by permanently deforming the springs. Another object of the invention is to provide an adjustable diaphragm in which spring forces applied to the user's body depend much less or not at all upon the diameter to which the diaphragm has been adjusted.

Other objects of the invention will in part be obvious and will in part appear hereinafter.

The invention accordingly comprises the features of construction, combination of elements, and arrangement of parts, which will be exemplified in the construction hereinafter set forth, and the scope of the invention will be indicated in the claims.

For a fuller understanding of the nature and objects of the invention reference should be had to the following detailed description taken in connection with the accompanying drawings, in which:

FIG. 6 is an enlarged section view taken at lines 6—6 in FIG. 3.

FIG. 7 is a diagrammatic cross-section view of a prior art diaphragm useful in understanding certain principles of the invention.

FIG. 8 illustrates one possible modification of the invention.

Figure 1:
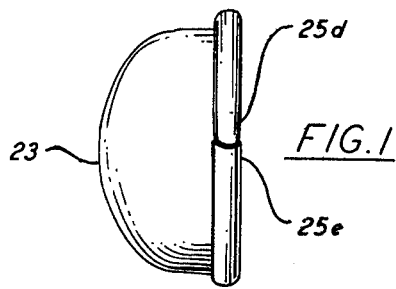
FIG. 1 is a side view of one form of adjustable diaphragm constructed in accordance with the invention.
Figure 2:
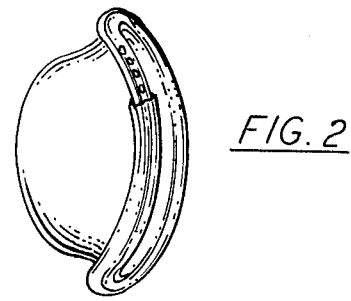
FIG. 2 is an isometric view illustrating the device of FIG. 1 slightly bent to the form in which it is inserted.

Referring to FIG. 7, the prior art diaphragm diagrammatically illustrated therein includes a thin elastomeric impermeable membrane or sheath portion 10 having an integral annular rim portion 11. As shown in U.S. Pat. Nos. 2,443,943 and 2,463,356, various forms of collapsible-expandable springs may be situated inside a hollow rim portion 11, to allow diameter adjustment. It is important to note that the rubber of the rim portion surrounding any such spring assembly comprises a given amount of bulk material. If such a diaphragm is compressed to a minimum usable diameter, it can be seen that the rubber comprising the rim portion inherently tends to wrinkle or buckle. Wrinkles are shown in FIG. 7 in exaggerated form at 12 and 13. If the spring assembly tends to fill the hollow passage within which it is situated, or is biased to stretch the rim portion 11, a wrinkle tends to occur outwardly as shown at 12, while an inward buckling may occur if, for example, the spring assembly does not substantially fill the hollow passage in the rim portion. In devices such as that shown in U.S. Pat. No. 2,463,356 wherein springs having different diameters around rim 11 are used, buckling or wrinkling also may occur at points where the diameter of the spring assembly changes. In FIG. 7 where thin flat spring ends 14 and 15 join a coil spring 16 of greater diameter, buckling may occur at points 17 and 18, for example. A problem tends to arise because such buckling or wrinkling may completely destroy the effectiveness of the diaphragm in blocking the passage of sperm. The present invention overcomes such a problem by provision of an outer ring assembly which telescopes into itself when its diameter is reduced, obviating any tendency for its outer perimeter to wrinkle or buckle.

Figure 4:
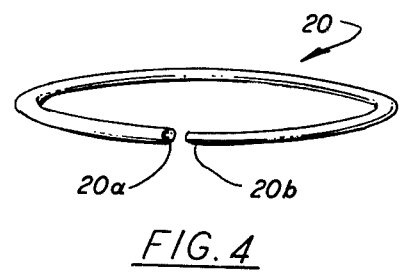
FIG. 4 is an isometric view of a telescoping inner ring portion of the device of FIG. 1.

Referring to FIG. 4 an inner ring piece of the pessary of the invention is shown as comprising a resilient plastic one-piece generally-solid, generally annular, split ring 20 having a recess 20a in one of its ends. Recess 20a is adapted to telescopingly and slidingly receive the other end 20b. Inner ring 20 can be formed of rubber or metal instead of plastic. In a typical application I contemplate that the diameter of ring 20 be variable between 50 mm. and 90 mm., and hence recess 20a is provided with a depth of about 126 mm. (0.5 inch) or more.

Figure 5:
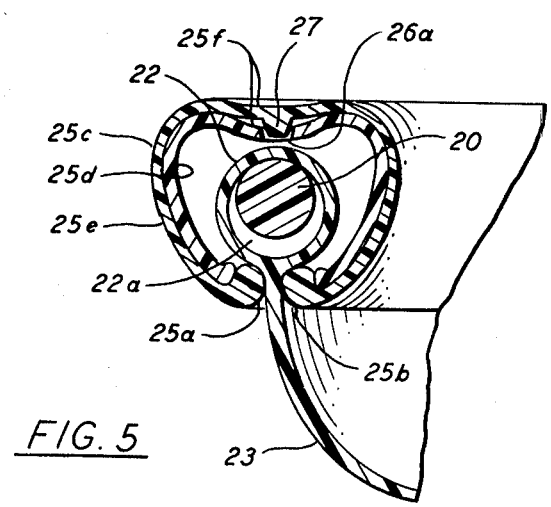
FIG. 5 is an enlarged cross-section view taken at lines 5—5 in FIG. 3.

An elastomeric (e.g. rubber) hollow rim 22 carrying an impermeable sheath portion 23 is formed to surround inner ring 20, as best seen in FIG. 5, with ring 20 free to slide within the hollow passage 22a within which it is situated. It can be seen that upon compression of ring 20 when it is inside hollow rim 22, the periphery of hollow rim 22 well may tend to wrinkle or buckle in the manner of the prior art devices discussed in connection with FIG. 7. However, because such wrinkles do not lie adjacent vaginal tissues, their existence cannot allow passage of sperm.

Figure 3:
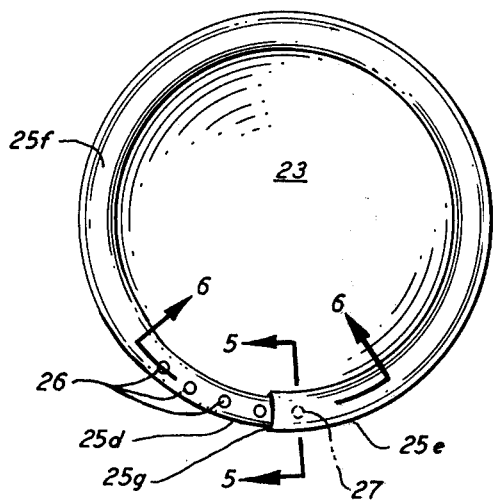
FIG. 3 is a top view of the device of FIG. 1.

As best seen in FIG. 5, the rim 22 carrying telescoping inner ring 20 is surrounded around its entire periphery by a resilient outer ring member 25 which clamps over rim 22. Outer ring member 25 is provided with a pair of rounded edges 25a, 25b which press against inner rim 22 on opposite sides of sheath portion 23 where sheath portion 23 joins rim 22. The crucial surface which engages vaginal tissue and which must not buckle or tend to wrinkle then becomes the diametrical extreme of outer ring member 25, substantially at point 25c in FIG. 5. This peripheral surface will not wrinkle or buckle when the device is adjusted to a small diameter because one end 25d of outer ring member 25 telescopes into its other end, 25e, as is apparent from FIGS. 3 and 5. The upper or outer surface of outer ring member 25 preferably is slightly concave as shown at 25f, and in the concavity near end 25d of ring 25 a plurality of narrow-mouthed recesses 26, 26 are located, spaced circumferentially apart, one such recess being shown at 26a in FIG. 5. End 25e of ring member 25 includes an internal bead or boss portion 27, thereon. When end 25d of ring 25 has been telescoped into end 25e to provide a desired diameter for the diaphragm, the bead or blade 27 is forced or snapped into one of the recesses 26 to lock the device at the desired diameter. Outer end 25e of outer ring member 25 preferably tapers to a thin edge at its extreme end at point 25g in FIG. 3, so that there is no appreciable ledge or sudden change in the outside diameter of the device, no matter the diameter to which the device has been adjusted.

It is vitally necessary that sperm not enter the space between rings 22 and 25 by passing rounded edge 25a, and then exiting into the cervix via one of holes 26 or past rounded edge 25b. To prevent such passage of sperm outer ring 25 is formed so that rounded edges 25a, 25b clamp the sheath 23 adjacent rim 22 with substantial clamping force. It is to be noted however, that the magnitude of the clamping force is not felt by the user, and indeed, once the device has been locked at a desired diameter, the forces which it applies to internal female tissues are substantially independent of the amount which the device has been compressed in order to achieve the desired diameter.

In the modified embodiment illustrated in FIG. 8, sheath 23' carries a plurality of soft nubs 23a, 23a molded integrally with the sheath on the bottom of the sheath, away from rim 22. Nubs 23a, 23a tend to provide increased sensation or stimulation to the sexual partner of the user of the invention.

It will thus be seen that the objects set forth above, among those made apparent from the preceding description, are efficiently attained, and since certain changes may be made in the above constructions without departing from the scope of the invention, it is intended that all matter contained in the above description or shown in the accompanying drawings shall be interpreted as illustrative and not in a limiting sense.

The embodiments of the invention in which an exclusive property or priviledge is claimed are defined as follows:

1. An adjustable diaphragm, comprising, in combination: a sheath member having a hollow annular rim portion; a resilient inner ring member disposed within said hollow rim portion with one end of said inner ring member telescoping into the other end of said inner ring member; and a resilient outer ring member surrounding said rim portion and clamping against said sheath member around the periphery of said rim portion on both sides of said sheath member, one end of said outer ring member telescoping into the other end of said outer ring member; and locking means on said outer ring member for fixing said outer ring member in any one of a plurality of discrete positions to fix the outer diameter of said diaphragm.

2. The diaphragm according to claim 1 wherein said locking means comprises a plurality of recesses spaced apart near one end of said outer ring member and a cooperating projecting boss carried near the other end of said outer ring member and adapted to be inserted into any one of said recesses.

3. The diaphragm according to claim 1 wherein said outer ring member is generally U-shaped in cross-section and provided with a pair of rounded edges resiliently urged toward each other on opposite sides of said sheath adjacent said annular rim portion.

4. An adjustable diaphragm, comprising, in combination: an impermeable sheath having an annular rim; resilient means situated within said rim and urging said rim to increase the diameter of said rim; and an outer ring member surrounding the outside of said annular rim and limiting diametrical expansion of said annular rim.

5. A diaphragm according to claim 4 wherein said outer ring member has a pair of ends, one of said ends being adapted to telescope into the other of said ends.

6. A diaphragm according to claim 4 wherein said outer ring member includes means for limiting diametrical expansion of said outer ring member to any one of a plurality of discrete diameters.

7. A diaphragm according to claim 4 wherein said outer ring member includes a pair of edges resiliently urged toward each other on opposite sides of said sheath adjacent said annular rim.

* * * * *